(12) United States Patent
Maillefer et al.

(10) Patent No.: US 7,906,107 B2
(45) Date of Patent: *Mar. 15, 2011

(54) HAIR WAX PRODUCTS WITH A LIQUID OR CREAMY CONSISTENCY

(75) Inventors: Sarah Maillefer, Middes (CH); Andre Rehmann, Schmitten (CH); Benedikt Zenhaeusern, Giffers (CH)

(73) Assignee: Wella AG, Darmstadt (DE)

(*) Notice: Subject to any disclaimer, the term of this patent is extended or adjusted under 35 U.S.C. 154(b) by 2245 days.

This patent is subject to a terminal disclaimer.

(21) Appl. No.: 10/628,060

(22) Filed: Jul. 25, 2003

(65) Prior Publication Data

US 2004/0052744 A1 Mar. 18, 2004

(30) Foreign Application Priority Data

Jul. 31, 2002 (DE) .................... 102 34 801

(51) Int. Cl.
*A61K 7/00* (2006.01)
*A61K 7/06* (2006.01)

(52) U.S. Cl. ....... 424/47; 424/70.1; 424/70.31; 424/400; 424/401

(58) Field of Classification Search .................. 424/497, 424/47, 70.1, 70.31, 400, 401
See application file for complete search history.

(56) References Cited

U.S. PATENT DOCUMENTS

| | | | |
|---|---|---|---|
| 5,306,488 A | | 4/1994 | Vanlerberghe et al. |
| 5,885,561 A * | | 3/1999 | Flemming et al. ............... 424/62 |
| 6,066,316 A | | 5/2000 | Shiojima et al. |
| 6,475,475 B2 * | | 11/2002 | Birkel et al. ............... 424/70.15 |
| 6,582,679 B2 * | | 6/2003 | Stein et al. ............... 424/47 |
| 6,585,965 B1 * | | 7/2003 | Carballada et al. ............ 424/70.1 |
| 6,649,154 B1 * | | 11/2003 | Yoshida et al. ............. 424/70.13 |
| 6,730,290 B2 * | | 5/2004 | Emmerling et al. ............ 424/47 |
| 6,733,790 B1 * | | 5/2004 | Garces Garces ............. 424/497 |
| 7,037,488 B2 * | | 5/2006 | Krause et al. ................. 424/70.1 |

FOREIGN PATENT DOCUMENTS

| | | |
|---|---|---|
| DE | 199 07 313 A1 | 8/2000 |
| DE | 100 57 353 A1 | 6/2001 |
| EP | 0 394 078 | 10/1990 |
| EP | 0 394 078 A1 | 10/1990 |
| EP | 0 868 898 A1 | 10/1998 |
| WO | 01/00147 A1 | 1/2001 |

OTHER PUBLICATIONS

E.W. Flick: "Cpsmetic and Toiletry Formulations, 2nd Ed." 1989, Noyes Publication, USA, XP002262392204660, pp. 26, 216, 218, 366, 378, 399, 420, 433, 475, 625.
Database Chamical Abstracts "Online!" Retrieved From STN Database Accession No. 136: 374 565 XP 002262394 & JP 2202 145758 A May 22, 2002.
M. Schlossman Ed.: "The Chemistry and Manufacture of Cosmetics . . ." 2000, Allured Pub. Corp., USA, XP002262393, p. 383.
Ullmanns' Encyclopedia of Industrial Chemistry (Ullmans Encyklopaedie Der Technischen Chemie), 4th Edition, vol. 24, p. 3.

* cited by examiner

*Primary Examiner* — Ardin Marschel
*Assistant Examiner* — Zohreh Vakili
(74) *Attorney, Agent, or Firm* — Michael J. Striker

(57) ABSTRACT

The hair wax product with liquid or creamy consistency for treating or setting up a human hairstyle contains at least 40% by weight of an aqueous or aqueous-alcoholic carrier medium, at least 5 percent by weight of an emulsifier and at least 2 percent by weight of wax. The weight ratio of emulsifier to wax is greater than 1, preferably 1.1 to 4. The invention also includes methods for styling and re-styling human hair-dos or hairstyles using the hair wax product according to the invention.

8 Claims, No Drawings

HAIR WAX PRODUCTS WITH A LIQUID OR CREAMY CONSISTENCY

CROSS-REFERENCE TO RELATED APPLICATIONS

This application claims priority under 35 U.S.C. 119(a)-(d) to German Patent Application No. 102 34 801.4, filed 31 Jul. 2002.

BACKGROUND OF THE INVENTION

1. Field of the Invention

The subject matter of the present invention is a wax product with a liquid or creamy consistency containing an aqueous or aqueous-alcoholic carrier medium, emulsifiers and waxes, in which the weight ratio of emulsifier to wax is greater than 1. The invention also relates to a process for setting up and again setting up a human hairstyle using the wax product according to the invention.

2. Description of Related Art

Hair wax compositions are known products for hair treatment. They particularly find application in putting short to medium length hair in a fashionable hairstyle and impart hold and luster as well as stabilize, condition and fix the hairstyle. They provide the hairstyle with shape and texture. Conventional hair wax has a waxy solid consistency and is usually provided in cups or other vessels. Its action is based on the following working principles. Product is removed with the fingers. The wax is distributed on the surface of the hand and then melted or at least considerably softened by the heat of the hand. It is possible to work the otherwise too hard wax into the hair because of this softening or melting. The wax is worked into the hair in a softened or more or less liquid state. Then it cools and again, reaches its original consistency. It hardens and the hairdo obtained has stability and hold and frequently a slightly wet look. The limits of the product performance of conventional styling wax products are established by these action principles. So that the wax may be worked into the hair to a sufficient extent, it must not be too hard to be removed with the hand, and the melting or softening point must be near the body temperature. On the other hand, only moderate product performance is attained regarding hair conditioning and hold and volume of the hairdo. In addition, the load on the hair is comparatively high. Of course an improved fixing and improved hold may be obtained with a harder wax composition, however the harder the wax, the harder is the product mass and the more difficult it is to process it and work it in the hair.

SUMMARY OF THE INVENTION

It is an object of the present invention to provide a hair wax product, which improves the hold and stability of the hairstyle, shapes the hair and imparts a natural silky luster, which forms no visible residue and is sufficiently washable, while at the same time is easily distributed on the hair and is satisfactorily worked into the hair.

It has now been found that these requirements are fulfilled by a hair wax product with a liquid or creamy consistency in a watery or watery-alcoholic base, which contains at least one emulsifier and at least one wax or waxy substance in a predetermined ratio.

Thus the hair wax product with a liquid or creamy consistency contains (A) at least 40% by weight of an aqueous or aqueous-alcoholic carrier medium;
(B) at least 5% by weight of at least one emulsifier; and
(C) at least 2 percent by weight of at least one wax;
wherein the weight ratio of emulsifier (B) to wax (C) is greater than 1 and preferably in a range of 1.1 to 4, especially preferably in a range of 1.5 to 3.

Hair wax products according to the invention are characterized by a special transient stickiness gradient during application. The hair has a comparatively high initial stickiness immediately after application, which lasts for a short time (e.g. for about 20 to 30 seconds). The high initial stickiness automatically falls to a residual stickiness. Because of the high initial stickiness the styling of the hair and the shaping of the hair-do is considerably simplified in comparison to commercial solid hair wax products and styling creams. A high stickiness of the treated hair would, if it would be permanent, generally be considered unpleasant and undesirable. The product changes into an only mildly sticky wax while acting on the hair because of the automatic decrease in its stickiness. The mild or slight residual stickiness provides a pleasant feel. It has the special advantage that restyling of the hair-do is always possible. Additional advantages of the product according to the invention include a problem-free application, a lustrous, not dull appearance of the hair and short drying times.

Hair wax products of the invention containing a wax, emulsifier and water are of course known according to the state of the art. The especially advantageous application properties of the product according to the invention are obtained however only with certain amounts and weight ratios of these ingredients. Also the emulsifier must be present in excess. Hair treatment agents are known from EP 394 078 A1 containing a micro-dispersion of wax in water. The amount ratio of wax to emulsifier is between 1 and 30. In other words, the wax is in excess. Too little emulsifier leads to hair, which is very dull and undesirably mat.

The term "creamy consistency" means the typical consistency of creams, i.e. of aqueous pasty preparations based on fats and waxes, water and emulsifiers. The term "liquid consistency" means the typical consistency of liquids having various different viscosity. It is understood to mean that the composition flows at room temperature (25° C.), i.e. it runs on an inclined plane (45°). The terms "wax", "waxy", "wax-like" relate especially to the definition for waxes according to Ullmanns' Encyclopedia of Industrial Chemistry (Ullmanns Encyklopädie der technischen Chemie), 4th Edition, Volume 24, p. 3. Accordingly waxes are plastic at 20° C., solid to brittle hard, coarse to fine crystalline, translucent to opaque, however they are not glassy. They melt over 40° C. without decomposition. They have comparatively low viscosity already a little above their melting point, a strongly temperature dependent consistency and solubility and can be polished with a gentle pressure. A hair wax product is a product, with which hair can be shaped into a hair-do or hairstyle because it contains at least one wax.

Carrier Medium (A)

The hair wax product according to the invention contains preferably from 40 to 90, especially preferably from 50 or from 60 to 80, percent by weight of the carrier medium (A). The carrier medium can comprise water or a mixture of water with at least one alcohol. Suitable alcohols are especially monohydric or polyhydric $C_1$- to $C_5$-alcohols, such as ethanol, n-propanol, isopropanol, butanols, pentanols, ethylene glycol, propylene glycol, butylene glycol, glycerol or pentandiols. Ethanol and isopropanol are preferred monohydric alcohols. Glycerol and propylene glycols are especially preferred as the polyhydric alcohols. The hair wax product preferably contains from 20 to 70, especially preferably 20 to 60, percent by weight water. Monohydric alcohols are preferably contained in the hair wax product according to the invention in an amount of 10 to 50, especially preferably from 15 to 40. Polyhydric alcohols are preferably contained in the hair wax product according to the invention in an amount of 0 to 10, especially preferably from 0.5 to 10, and even more preferably from 1 to 5, percent by weight. The drying speed and thus the duration of the strongly adhesive or sticky phase can be adjusted to the desired extent by variation of the amount of volatile alcohol, such as ethanol or isopropanol, in the hair wax product.

A content of alcohol not only causes a reduction in the drying time but also a reduction in the residual stickiness remaining after drying. In a preferred embodiment the hair wax product according to the invention contains from 20 to 60 percent by weight water, from 10 to 50 percent by weight of at least one monohydric $C_2$- to $C_3$-alcohol, preferably ethanol, and from 0.5 to 10 percent by weight of at least one polyhydric $C_2$- to $C_5$-alcohol. The weight ratio of water to monohydric alcohol is preferably in a range of 0.5 to 5, especially preferably from 1 to 3.

Emulsifier (B)

The hair wax product according to the invention contains preferably from 5 to 40, especially preferably from 10 to 30, percent by weight of the emulsifier (B). Suitable emulsifiers and emulsifier mixtures are especially those with an HLB value of at least 10, especially of 10 to 20, especially preferably of about 13 to about 17. The emulsifier can be nonionic, anionic, cationic or zwitterionic. The nonionic emulsifiers are preferred. Suitable emulsifiers are, e.g.:

ethoxylated fatty alcohols, fatty acids, fatty acid glycerides or alkyl phenols, especially addition products of 2 to 30 mol ethylene oxide and/or 1 to 5 mol propylene oxide to $C_8$- to $C_{22}$-fatty alcohols, to $C_{12}$- to $C_{22}$-fatty acids or alkylphenols with 8 to 15 C-atoms in the alkyl groups;

$C_{12}$- to $C_{22}$-fatty acid monoesters and diesters of addition products of 1 to, 30 mol ethylene oxide to glycerol;

addition products of 5 to 60 mol ethylene oxide to castor oil or hydrogenated castor oil;

mono-, di- and/or triesters of phosphoric acid with addition products of 2 to 30 mol ethylene oxide to $C_8$- to $C_{22}$-fatty alcohols;

fatty acid sugar esters, especially esters of sucrose and one or two $C_8$- to $C_{22}$-fatty acids, INCI names: sucrose cocoate, sucrose dilaurate, sucrose distearate, sucrose laurate, sucrose myristate, sucrose oleate, sucrose palmitate, sucrose ricinoleate, sucrose stearate;

polyglyceryl fatty acid esters, especially one, two or more $C_8$- to $C_{22}$-fatty acid and polyglycerol with 2 to 20 glyceryl units.

In an especially preferred embodiment the emulsifiers have a waxy consistency and a dripping point above 25° C.

Wax (C)

The hair wax product according to the invention contains preferably a range of 2.5 to less than 40 percent by weight, especially preferably from 5 to less than 30 percent by weight, of wax (C). Every known wax and/or wax-like substance in the state of the art can in principle be used. These waxes and wax-like substances include animal, vegetable, mineral and synthetic waxes, micro-crystalline waxes, macro-crystalline waxes, solid paraffins petrolatum, VASELINE®, ozocerite, montan wax, Fischer-Tropsch wax, polyolefin waxes, such as polybutene, beeswax, wool wax and its derivatives, such as wool wax, alcohols, candelilla wax, carnauba wax, Japan wax, hardened fats, fatty acid esters and fatty acid glycerides with a hardening point of above 40° C., polyethylene waxes and silicone waxes. Those materials are suitable as waxes, which have waxy properties, especially a solidification point above 40° C., preferably above 55° C. The needle penetration number (0.1 mm, 100 g, 5 s, 25° C., according to DIN 51 579) is preferably in a range of 2 to 0.70, especially of 3 to 40. Preferably the hair wax product contains at least one wax, which has a needle penetration point of less than 40, especially preferably less than 20. Carnauba wax and ceresin with a needle penetration number less than 20 and their mixtures are especially preferred.

Additional Oils (D)

In an especially preferred embodiment, especially for making creamy products with improved soft feel, the hair wax product according to the invention contains additionally at least one hydrophobic substance (D), which is liquid at room temperature (25° C.), especially at least one oil. A hair wax product according to the invention contains preferably from 0.1 to 20 percent by weight, especially preferably from 1 to 10 percent by weight, of the hydrophobic liquid (D). This hydrophobic substance can be an easily volatilized or not-so-easily-volatilized substance, such as oil that is difficult to volatilize. The easily volatilized hydrophobic substances are liquid at room temperature and have a boiling point in a range of preferably 30° C. to 250° C., especially preferably from 60° C. to, 220° C. Liquid hydrocarbons, liquid cyclic or linear silicones (dimethylpolysilioxanes) or mixtures of the foregoing substances are suitable. Suitable hydrocarbons include paraffins or isoparaffins with 5 to 14 carbon atoms, especially preferably with 8 to 12 carbon atoms, especially dodecane or isododecane. Suitable liquid, easily volatilized silicones include cyclodimethylsiloxanes with 3 to 8, preferably 4 to 6 silicon atoms, especially cyclotetradimhethylsiloxane, cyclopentadimethylsiloxane or cyclohexadimethylsiloxane. Furthermore dimethylsiloxane/methylalkylsiloxane cyclocopolymers, e.g. Silicone FZ 3109 of Union Carbide, which is a dimethylsiloxane/methyloctylsiloxane cyclocopolymer, are suitable. Suitable volatile linear silicones have from 2 to 9 Si atoms. Hexamethyldisiloxanes or alkyltrisiloxanes; such as hexylheptamethyltrisiloxane or octylheptamethyltrisiloxane, are also suitable. The non-volatile hydrophobic oils have a melting point of under 25° C. and a boiling point of over 250° C., preferably over 300° C. In principle generally oils known to those skilled in the art can be used. These oils include vegetable or animal oils, mineral oils, silicone oils or their mixtures. Suitable silicone oils include polydimethylsiloxanes, phenylated silicones, polyphenylmethylsiloxanes, phenyltrimethicones, poly($C_1$- to $C_{20}$)alkylsiloxanes, alkylmethylsiloxanes. Furthermore hydrocarbon oils, such as paraffin or isoparaffin oils, squalene, oils from fatty acids and polyoils, especially triglycerides of $C_{10}$- to $C_{30}$-fatty acids, are suitable. Suitable vegetable oils include sunflower seed oils, coconut oil, castor oil, lanolin oil, jojoba oil, corn oil and soya oil. Hydrocarbon oils, especially mineral oils (paraffinum liquidum) and vegetable oils and fatty acid triglycerides, are especially preferred as the oils.

In a preferred embodiment the hair wax product according to the invention contains (A) 40 to 90 percent by weight of an aqueous-alcoholic carrier medium, which contains from 20 to 60 percent by weight water, from 10 to 50 percent by weight ethanol and/or isopropanol, and from 0 to 10 percent by weight of a dihydric or trihydric $C_2$- to $C_3$-alcohol, wherein a weight ratio of water to ethanol and/or isopropanol is in a range of 0.5 to 5;

(B) from 10 to 30 percent by weight of at least one nonionic emulsifier;
(C) from 5 to 30 percent by weight of at least one wax, and
(D) from 0 to 20 percent by weight of at least one hydrophobic liquid oil;
wherein the weight ratio of emulsifier (B) to wax (C) is in a range of 1.5 to 3.

In addition to the above-stated ingredients the hair wax product according to the invention can contain additional conventional cosmetic additive ingredients as follows:

cosmetic dye stuffs in an amount of up to 6 percent by weight, preferably 0.1 to 4 percent by weight, e.g. C.I. Pigment Red 4 (C.I. 12 085), C.I. Pigment Green (C.I. 74 260), and/or C.I. Vat Blue 4 (C.I. 69 800);

pearlescence pigments in an amount of up to 25 percent by weight, preferably from 1 to 20 percent by weight, e.g. such as those on a titanium dioxide mica basis;

perfume and fragrance substances in an amount of up to 2 percent by weight, preferably from 0.01 to 1 percent by weight;

light protective and preservative agents in an amount of up to 1 percent by weight, preferably from 0.01 to 0.5 percent by weight, e.g. parahydroxybenzoic acid ester, benzoic acid, silicylic acid, sorbic acid, mandelic acid, polyhexmethylene biguanidine hydrochloride or isothiazolinone derivative compounds;

film-forming polymers, e.g. polyvinyl pyrrolidone or vinylpyrrolidone/vinyl acetate copolymers in an amount of up to 5 percent by weight, preferably 0.1 to 4 percent by weight; and hair care additives, such as e.g. betaine, panthenol in an amount of up to 5 percent by weight, preferably from 0.01 to 4 percent by weight.

Application and Packaging

The hair wax product according to the invention can be filled according to its consistency in a suitable container or package, e.g. pans, tubes, bottles or other containers. The package or container can be provided with a pump apparatus, e.g. a mechanically driven pump dispenser for application of the product mass. The package or container can be provided with a device for making foam or a device for spraying, such as a mechanically operated pump foaming device or a mechanically operated spray pump for dispensing the product mass in the form of a foam or spray. The hair wax product however must have a consistency adapted to form a spray if it is to be applied with a spraying device. The mechanical pump, spraying device or foaming device for the hair wax product according to the invention can be a commercial pump or a commercial foam and/or spray head.

An especially preferred embodiment of the hair wax product is a product for hair treatment, in which a composition according to the invention together with a suitable propellant is filled in a pressure-resistant container which is provided with a device for producing foam (foam head). Suitable propellants include liquid propellants, such as propane, n-butane, isobutane, fluorinated hydrocarbons, such as 1,1-difluoroethane or 1,1,2-tetrafluoroethane, or dimethyl ether. These propellant gases can be used individually or in mixture, e.g. a mixture of propane and/or butane and dimethyl ether. A mixture of propane and butane is especially preferred. Typical filling ratios are in a range of about 80 to 98% by weight effective mixture to 2 to 20 percent by weight propellant. The pressure-resistant container can be made from any material known for aerosol spray or foam products. Suitable materials especially are metals, such as aluminum or tinplate. Commercial spray heads are used as a spray head.

Manufacture

The product according to the invention can be made by a method in which the wax components are melted and emulsified with the remaining ingredients in the aqueous carrier medium. Easily volatile ingredients are added after cooling and mixed. Subsequently the still liquid mass is filled into the desired container. In case of a propellant-containing product the propellant gas is subsequently added and the container is provided with a suitable foam head.

Application Process

The method of shaping or fashioning the hair-do with the hair wax product is also a part of the present invention. In this method the hair wax product is applied to dry or slightly moist hair and the desired hairstyle is set up during the temporary strongly sticky stage. The amount used is a pea-sized or hazelnut-sized quantity according to the hair length and desired effect, which advantageously is ground on the hand surface prior to application to the hair. Because of the special liquid or creamy consistency the product may be removed and distributed easily on the hair without great effort. The hair wax product provides hair stability, definition, structure, and, in spite of the soft and liquid consistency, a strong hold is provided to the hair. The hair has a pleasing appearance and appears especially neither, dull nor oily. The product is outstandingly suitable for creating styling and re-styling of modern hairstyles.

A method for re-shaping or re-styling a hairstyle according to the invention, in which a first hairstyle is established or set up with the above-described method and at a later time point during the stage characterized by the weak residual stickiness the first hairstyle is changed into a second hairstyle. The following examples should serve to illustrate the subject matter according to the invention.

EXAMPLES

Example 1

The following table I lists the composition of five examples, 1A to 1E, of hair wax products. The amounts of the ingredients in the table are given in grams.

| Ingredient | 1A | 1B | 1C | 1D | 1E |
|---|---|---|---|---|---|
| Carnauba wax | 5 | 10 | 10 | 10 | 15 |
| CREMOPHOR ® CO60[1] | 10 | 20 | 20 | 10 | 5 |
| MIWAGOL ® V[2] | — | — | 2.5 | — | — |
| Glycerol (86%) | — | — | 2.5 | — | — |
| Ethanol (94.7%) | 35 | 35 | 30 | 35 | 50 |
| Water | To 100 | To 100 | To 100 | To 100 | To 100 |

[1]INCI name: PEG-60 hydrogenated castor oil
[2]INCI name: Caprylic/capric triglyceride The exemplary compositions 1A, 1B and 1C have an excess of emulsifier and their properties were compared with those of the exemplary compositions 1D and 1E.

| | |
|---|---|
| 1A: | liquid consistency; good, but weak styling properties (soft-styling variant) |
| 1B: | thickened liquid, viscose consistency; good styling properties, good shapability of the hair, strong fixing (extra strong variant). |
| 1C: | creamy, pleasant soft consistency; very good shapabiility of the hair, very good styling properties. |

| | |
|---|---|
| 1D: | thickened liquid, viscose, gel-like consistency; too sticky. |
| 1E: | thin-liquid emulsion; too sticky, dull appearance of the hair. |

Example 2

Wax Cream

| | |
|---|---|
| 20 g | PEG-60 hydrogenated Castor Oil |
| 10 g | Carnauba Wax |
| 2.5 g | Glycerol (86%) |
| 2.5 g | Caprylic/capric triglyceride |
| 0.1 g | D-panthenol |
| q.s. | Preservative, UV-filter, perfumes |
| 29 g | Ethanol (94.7%) |
| to 100 g | Water |

Example 3

Wax Cream

| | |
|---|---|
| 10 g | PEG-60 hydrogenated Castor Oil |
| 15 g | PEG-40 hydrogenated Castor Oil, 90% |
| 10 g | Carnauba Wax |
| 2.5 g | Glycerol (86%) |
| 2.5 g | Caprylic/capric triglyceride |
| 0.1 g | D-panthenol |
| q.s. | Preservative, UV-filter, perfumes |
| 4 g | Ethanol (94.7%) |
| to 100 g | Water |

Example 4

Aerosol Hair Wax Foam Compositions 4A and 4B

| Ingredient | 4A | 4B |
|---|---|---|
| Carnauba wax | 10 | 10 |
| CREMOPHOR ® CO60[1] | 20 | — |
| Sucrose cocoate (92.5%) | — | 5 |
| Polyglyceryl-10 distearate | — | 5 |
| Ceteareth-20 | — | 5 |
| Oleth-20 | — | 5 |
| MIWAGOL ® V[2] | 2.5 | — |
| Glycerol (86%) | 2.5 | 2.5 |
| Octyldodecanol | — | 2.5 |
| PHB Propyl ester | 0.2 | 0.2 |
| PHB Methyl ester | 0.2 | 0.2 |
| Benzoic acid | 0.2 | 0.2 |
| D-panthenol | 0.1 | 0.1 |
| Methoxycinnamic acid octyl ester | 0.05 | 0.05 |
| Perfume | 0.1 | 0.1 |
| Ethanol (94.7%) | 19.15 | 29.15 |
| Water | To 100 | To 100 |

The composition was filled into a pressure-resistant aluminum aerosol can in a ratio of 92 percent by weight of effective ingredient mixture to 8 percent by weight propane/butane (4.8 bar) and provided with a foam head.

The amounts in the table II above are in grams.

The disclosure in German Patent Application 102 34 801.4 of Jul. 31, 2002 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a hair wax product with a liquid or creamy consistency, it is not intended to be limited to the details shown, since various modifications and changes may be made without departing in any way from the spirit of the present invention.

Without further analysis the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of shaping or styling hair in a hairstyle, said method comprising the steps of:
a) providing a hair wax composition containing from 20 to 60 percent by weight water; from 10 to 50 percent by weight of at least one monohydric alcohol with 2 to 3 carbon atoms; from 0 to 5 percent by weight of at least one polyhydric alcohol with 2 to 5 carbon atoms; from 10 to 30 percent by weight of at least one nonionic emulsifier and from 5 to 30 percent by weight of at least one wax; wherein the weight ratio of said at least one nonionic emulsifier to said at least one wax is greater than 1, so that a stickiness of said hair wax composition changes after application to dry or slightly wet hair to be shaped;
b) applying said hair wax composition to the dry or slightly wet hair to be shaped; and
c) within an initial time interval immediately after the applying of step b) in which said hair wax composition applied to the hair is more sticky than during a time after said initial time interval, putting the dry or slightly wet hair to be shaped into said hairstyle.

2. The method as defined in claim 1, wherein said at least one wax is an animal wax, a vegetable wax, a mineral wax, a synthetic wax, a micro-crystalline wax, a macro-crystalline wax, a solid paraffin, petrolatum, ozocerite, montan wax, Fischer-Tropsch wax, polyolefin wax, beeswax, wool wax, a wool wax alcohol, candelilla wax, carnauba wax, Japan wax, a hardened fat, fatty acid ester, a fatty acid glyceride with a hardening point of above 40° C. or a silicone wax, or any two or more of the aforesaid.

3. The method as defined in claim 1, further comprising restyling or reshaping the hairstyle by putting the hair in another desired hairstyle at said time after putting the hair in the desired hair style and during another phase in which the hair wax composition is comparatively less sticky than in said initial time interval.

4. The method as defined in claim 1, wherein said at least one nonionic emulsifier is
an addition product of 2 to 30 mol ethylene oxide and/or 1 to 5 mol propylene oxide to a $C_8$- to $C_{22}$-fatty alcohol, to a $C_{12}$- to $C_{22}$-fatty acid or an alkylphenol with 8 to 15 carbon atoms in the alkyl groups;
a $C_{12}$- to $C_{22}$-fatty acid mono-ester and/or -diester of an addition product of 1 to 30 mol ethylene oxide to glycerol;

an addition product of 5 to 60 mol ethylene oxide to castor oil or hydrogenated castor oil;

a mono-, di- and/or triester of phosphoric acid with an addition product of 2 to 30 mol ethylene oxide to a $C_8$- to $C_{22}$-fatty alcohol; or a mixture of any two of the aforesaid.

5. The method as defined in claim 1, wherein said initial time interval is from 20 to 30 seconds.

6. The method as defined in claim 1, wherein said at least one monohydric alcohol is selected from the group consisting of ethanol, n-propanol and isopropanol, and wherein said at least one polyhydric alcohol is glycerol.

7. The method as defined in claim 1, wherein said hair wax composition contains from 1 to 10 percent by weight of at least one hydrophobic oil.

8. The method as defined in claim 1, wherein said weight ratio of said at least one nonionic emulsifier to said at least one wax is from 1.1 to 4.

\* \* \* \* \*